US009492375B2

(12) United States Patent
Scifert

(10) Patent No.: US 9,492,375 B2
(45) Date of Patent: Nov. 15, 2016

(54) FOAM CARRIER FOR BONE GRAFTING

(75) Inventor: Jeffrey L. Scifert, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1139 days.

(21) Appl. No.: 12/178,497

(22) Filed: Jul. 23, 2008

(65) Prior Publication Data
US 2010/0021518 A1 Jan. 28, 2010

(51) Int. Cl.
*A61K 9/16* (2006.01)
*A61K 38/18* (2006.01)
*A61K 9/00* (2006.01)
*A61K 9/12* (2006.01)
*A61L 27/14* (2006.01)
*A61L 27/56* (2006.01)

(52) U.S. Cl.
CPC ............ *A61K 9/0024* (2013.01); *A61K 9/122* (2013.01); *A61K 9/1629* (2013.01); *A61K 38/1875* (2013.01); *A61L 27/14* (2013.01); *A61L 27/56* (2013.01); *A61L 2430/02* (2013.01)

(58) Field of Classification Search
CPC ................ A61K 9/0024; A61K 9/122; A61K 9/1639; A61K 38/1875; A61L 27/14; A61L 27/56; A61L 2430/02
USPC ..................... 424/423; 514/12, 1.1
See application file for complete search history.

(56) References Cited

U.S. PATENT DOCUMENTS

| 4,624,255 | A | 11/1986 | Schenck et al. |
| 4,863,457 | A | 9/1989 | Lee |
| 5,385,887 | A * | 1/1995 | Yim et al. ............ 514/12 |
| 5,522,844 | A | 6/1996 | Johnson |
| 5,681,873 | A | 10/1997 | Norton et al. |
| 5,868,789 | A | 2/1999 | Huebner |
| 6,030,967 | A | 2/2000 | Marui et al. |
| 6,069,129 | A | 5/2000 | Sandberg et al. |
| 6,179,862 | B1 | 1/2001 | Sawhney |
| 6,287,588 | B1 | 9/2001 | Shih et al. |
| 6,331,311 | B1 | 12/2001 | Brodbeck et al. |
| 6,428,804 | B1 | 8/2002 | Suzuki et al. |
| 6,432,063 | B1 | 8/2002 | Marcus |
| 6,461,631 | B1 | 10/2002 | Dunn et al. |
| 6,491,651 | B1 | 12/2002 | Leahy et al. |
| 6,589,549 | B2 | 7/2003 | Shih et al. |
| 6,630,155 | B1 | 10/2003 | Chandrashekar et al. |
| 6,632,457 | B1 | 10/2003 | Sawhney |
| 6,696,073 | B2 | 2/2004 | Boyce et al. |
| 6,756,058 | B2 | 6/2004 | Brubaker et al. |
| 6,773,714 | B2 | 8/2004 | Dunn et al. |
| 6,863,694 | B1 | 3/2005 | Boyce et al. |
| 6,867,240 | B2 * | 3/2005 | Ma et al. ............ 521/85 |
| 6,869,445 | B1 * | 3/2005 | Johnson ............ 623/17.11 |
| 6,974,462 | B2 | 12/2005 | Sater |
| 7,001,892 | B1 | 2/2006 | Chmielewski et al. |
| 7,144,412 | B2 | 12/2006 | Wolf et al. |
| 7,166,570 | B2 | 1/2007 | Hunter et al. |
| 7,214,371 | B1 * | 5/2007 | Cohen et al. ............ 424/93.7 |
| 7,220,281 | B2 | 5/2007 | Lambrecht et al. |
| 7,229,441 | B2 | 6/2007 | Trieu et al. |
| 7,235,043 | B2 | 6/2007 | Gellman et al. |
| 7,273,896 | B2 | 9/2007 | Daniloff et al. |
| 7,309,232 | B2 | 12/2007 | Rutherford et al. |
| 7,318,840 | B2 | 1/2008 | McKay |
| 7,329,259 | B2 | 2/2008 | Cragg |
| 7,361,168 | B2 | 4/2008 | Makower et al. |
| 7,365,165 | B2 | 4/2008 | Dix et al. |
| 7,367,978 | B2 | 5/2008 | Drewry et al. |
| 7,449,019 | B2 | 11/2008 | Uchida et al. |
| 7,462,155 | B2 | 12/2008 | England |
| 7,482,174 | B2 | 1/2009 | Kiefer et al. |
| 2001/0014831 | A1 | 8/2001 | Scarborough |
| 2002/0009454 | A1 | 1/2002 | Boone et al. |
| 2002/0081729 | A1 * | 6/2002 | Peters et al. ............ 435/406 |
| 2002/0082694 | A1 | 6/2002 | McKay |
| 2002/0090398 | A1 | 7/2002 | Dunn et al. |
| 2003/0109934 | A1 * | 6/2003 | Lewandrowski et al. . 623/23.59 |
| 2003/0133967 | A1 | 7/2003 | Ruszczak et al. |
| 2003/0204191 | A1 | 10/2003 | Sater et al. |
| 2003/0236573 | A1 | 12/2003 | Evans et al. |
| 2004/0072799 | A1 | 4/2004 | Li et al. |
| 2004/0082540 | A1 | 4/2004 | Hermida Ochoa |
| 2004/0167637 | A1 | 8/2004 | Biscup |
| 2004/0192658 | A1 | 9/2004 | Hunter et al. |
| 2004/0214793 | A1 | 10/2004 | Hermida Ochoa |
| 2004/0249463 | A1 | 12/2004 | Bindseil et al. |
| 2005/0025809 | A1 | 2/2005 | Hasirci et al. |
| 2005/0065214 | A1 | 3/2005 | Kronenthal |
| 2005/0079155 | A1 * | 4/2005 | Marshall ............ 424/85.2 |
| 2005/0142163 | A1 | 6/2005 | Hunter et al. |

(Continued)

FOREIGN PATENT DOCUMENTS

WO       03005961       1/2003

OTHER PUBLICATIONS

Welsh, JBJS, Surgical Implants, 1971.*
Oldham, Journal of Biomechanical Engineering, 2000.*
Melton, Journal of Bone and Mineral Research, vol. 12, 1997.*
Wozney, Journal of Cell Science, sup 13, 1990.*
PLGA density, 2013.*

(Continued)

Primary Examiner — Susan Tran
Assistant Examiner — William Craigo
(74) Attorney, Agent, or Firm — Sorell Lenna & Schmidt LLP

(57) ABSTRACT

An improved osteogenic composition is provided. The composition comprises a foam that contains polymer beads having one or more growth factors such as bone morphogenic protein. Through use of this composition, bone, collagen and/or other tissue growth may be facilitated.

16 Claims, No Drawings

(56) References Cited

U.S. PATENT DOCUMENTS

| | | |
|---|---|---|
| 2005/0186261 A1 | 8/2005 | Avelar et al. |
| 2005/0197293 A1 | 9/2005 | Mellis et al. |
| 2006/0002978 A1* | 1/2006 | Shea et al. .................. 424/426 |
| 2006/0079773 A1 | 4/2006 | Mourad et al. |
| 2006/0083730 A1* | 4/2006 | Kusanagi et al. .......... 424/94.1 |
| 2006/0106361 A1 | 5/2006 | Muni et al. |
| 2006/0148903 A1 | 7/2006 | Burch et al. |
| 2006/0189944 A1 | 8/2006 | Campbell et al. |
| 2006/0247772 A1 | 11/2006 | McKay |
| 2006/0270037 A1 | 11/2006 | Kato et al. |
| 2006/0287676 A1 | 12/2006 | Prajapati et al. |
| 2007/0048382 A1 | 3/2007 | Meyer et al. |
| 2007/0077267 A1 | 4/2007 | Molz et al. |
| 2007/0098756 A1* | 5/2007 | Behnam ....................... 424/423 |
| 2007/0156180 A1 | 7/2007 | Jaax et al. |
| 2007/0185367 A1 | 8/2007 | Abdou |
| 2007/0185497 A1 | 8/2007 | Cauthen et al. |
| 2007/0202074 A1 | 8/2007 | Shalaby |
| 2007/0218424 A1 | 9/2007 | Vuorisalo et al. |
| 2007/0243225 A1 | 10/2007 | McKay |
| 2007/0243228 A1 | 10/2007 | McKay |
| 2007/0259019 A1 | 11/2007 | McKay |
| 2007/0260325 A1 | 11/2007 | Wenz |
| 2008/0008988 A1 | 1/2008 | McKay et al. |
| 2008/0015140 A1 | 1/2008 | Kuzmin et al. |
| 2008/0019969 A1 | 1/2008 | Gorman |
| 2008/0019970 A1 | 1/2008 | Gorman |
| 2008/0019975 A1 | 1/2008 | Gorman |
| 2008/0091207 A1 | 4/2008 | Truckai et al. |
| 2008/0109007 A1 | 5/2008 | Schwager et al. |
| 2008/0147197 A1 | 6/2008 | McKay |
| 2008/0175911 A1 | 7/2008 | McKay et al. |
| 2008/0213283 A1 | 9/2008 | Olmarker et al. |
| 2008/0294261 A1 | 11/2008 | Pauza et al. |
| 2008/0317805 A1 | 12/2008 | McKay et al. |
| 2009/0024135 A1 | 1/2009 | Triplett et al. |

OTHER PUBLICATIONS

Woo, Pharmaceutical Research, 18, 12, 2001.*
U.S. Appl. No. 12/194,432, filed Aug. 19, 2008.
U.S. Appl. No. 12/193,794, filed Aug. 19, 2008.

* cited by examiner

FOAM CARRIER FOR BONE GRAFTING

BACKGROUND

Bone is a composite material that is composed of impure hydroxyapatite, collagen and a variety of non-collagenous proteins, as well as embedded and adherent cells. Due to disease, a congenital defect or an accident, a person may lose or be missing part or all of one or more bones or regions of cartilage in his or her body, and/or have improper growth or formation of bone and/or cartilage.

Mammalian bone tissue is known to contain one or more proteinaceous materials that are active during growth and natural bone healing. These materials can induce a developmental cascade of cellular events that results in bone formation. Typically, the developmental cascade of bone formation involves chemotaxis of mesenchymal cells, proliferation of progenitor cells, differentiation of cartilage, vascular invasion, bone formation, remodeling and marrow differentiation.

When bone is damaged, often bone grafting procedures are performed to repair the damaged bone especially in cases where the damage is complex, poses a significant risk to the patient, and/or fails to heal properly. Bone grafting is also used to help fusion between vertebrae, correct deformities, or provide structural support for fractures of the spine. In addition to fracture repair, bone grafting is also used to repair defects in bone caused by birth defects, traumatic injury, or surgery for bone cancer.

There are at least three ways in which a bone graft can help repair a defect. The first is called osteogenesis, the formation of new bone within the graft. The second is osteoinduction, a process in which molecules contained within the graft (e.g., bone morphogenetic proteins) convert the patient's cells into cells that are capable of forming bone. The third is osteoconduction, a physical effect by which the matrix of the graft forms a scaffold on which cells in the recipient are able to form new bone.

The source of bone for grafting can be obtained from bones in the patient's own body (e.g., hip, skull, ribs, etc.), called autograft, or from bone taken from other people that is frozen and stored in tissue banks, called allograft. The source of bone may also be derived from animals of a different species called a xenograft.

Some grafting procedures utilize a variety of natural and synthetic replacement materials instead of bone (e.g., collagen, silicone, acrylics, hydroxyapatite, calcium sulfate, ceramics, etc.).

To place the graft, the surgeon makes an incision in the skin over the bone defect and shapes the bone graft or replacement material to fit into the defect. As persons of ordinary skill are aware, growth factors (e.g., bone morphogenic protein-2) may be introduced into a patient in order to spur the patient's body to begin the formation of new bone and/or cartilage.

In order to increase the effectiveness of growth factors it may be desirable to introduce them in certain formulations that help to control release profiles. It may also be advantageous to design scaffoldings that provide frameworks on which the new bone or cartilage can grow.

No formulations or scaffoldings are ideal for all applications. Thus, there is a need to develop new formulations and scaffoldings.

SUMMARY

Compositions and methods are provided that promote osteogenic growth. Through the use of these compositions, the growth of bone, cartilage and/or related tissue may be facilitated particularly in cranio-maxillofacial procedures. In some embodiments, the compositions and methods provided allow for delivery of one or more growth factors to the target tissue site with little or no unwanted migration of the growth factor away from the target tissue site. In some embodiments, the composition and methods provided utilize a foam that confines the growth factor to the target tissue site and also functions as a pliant, compression resistant scaffold for bone, cartilage and/or related tissue growth. In some embodiments, the foam can resist compression forces that often occur during or after cranio-maxillofacial procedures.

In some embodiments, the present application provides an osteogenic composition for implantation at or near a target tissue site, the osteogenic composition comprising: a polymeric bead for delivering a growth factor at or near the target tissue site, the polymeric bead comprising the growth factor; and a porous foam for confining the polymeric bead at or near the target tissue site, the porous foam containing a plurality of pores having a size between about 100 micrometers and about 350 micrometers at their widest points.

In some embodiments, the present application provides an osteogenic composition for implantation at or near a target tissue site, the osteogenic composition comprising one or more polymeric beads containing an effective amount of growth factor; the one or more polymeric beads being less than 3.0 mm in diameter and adapted to deliver the growth factor at or near the target tissue site; and a porous foam for confining the one or more polymeric beads at or near the target tissue site, the porous foam containing a plurality of pores having a size of between about 100 micrometers and about 350 micrometers to allow tissue growth at the target tissue site.

In some embodiments, the present application provides a method for accelerating repair in a patient in need of such treatment, the method comprising the step of implanting at a target tissue site in need of replacement bone, an osteogenic composition comprising: a porous foam, wherein said porous foam contains a plurality of pores between about 100 micrometers and about 350 micrometers at their widest points; and a bead, wherein said bead comprises a growth factor, and a polymer.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this invention belongs.

Unless explicitly stated or apparent from context, the following terms are phrases have the definitions provided below:

DEFINITIONS

It is noted that, as used in this specification and the appended claims, the singular forms "a," "an," and "the," include plural referents unless expressly and unequivocally limited to one referent. Thus, for example, reference to "a drug bead" includes one, two, three or more drug beads.

The term "biodegradable" includes that all or parts of the drug bead and/or foam will degrade over time by the action of enzymes, by hydrolytic action and/or by other similar mechanisms in the human body. In various embodiments, "biodegradable" includes that a bead (e.g., microparticle, microsphere, etc.) and/or foam can break down or degrades within the body to non-toxic components after or while a therapeutic agent has been or is being released. By "bioerodible" it is meant that the bead and/or foam will erode or degrade over time due, at least in part, to contact with substances found in the surrounding tissue, fluids or by cellular action. By "bioabsorbable" it is meant that the osteogenic composition will be broken down and absorbed within the human body, for example, by a cell or tissue. "Biocompatible" means that the bead and/or foam will not cause substantial tissue irritation or necrosis at the target tissue site.

A "bead" includes but is not limited to capsules, microspheres, microparticles, microcapsules, microfibers, nanospheres, nanoparticles, matrices, pills, pellets, or other pharmaceutical delivery compositions or a combination thereof. Suitable materials for the bead are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof.

The "foam" of the present application is utilized as a scaffold for bone and/or cartilage repair, regeneration, and/or augmentation. In some embodiments, the foam is a colloid. The foam comprises a biocompatible material and has an open celled microstructure. Typically, the foam provides a 3-D matrix of interconnecting pores, which acts as a pliant, compression resistant scaffold for cell migration. The morphology of the scaffold guides cell migration and cells are able to migrate into or over the scaffold, respectively. The cells then are able to proliferate and synthesize new tissue and form bone and/or cartilage. Like the bead, the foam may be made from biodegradable, bioabsorbable, and/or biocompatible material.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The term "mammal" refers to organisms from the taxonomy class "mammalian," including but not limited to humans, other primates such as chimpanzees, apes, orangutans and monkeys, rats, mice, cats, dogs, cows, horses, etc.

The phrase "osteogenic composition" refers to a composition that comprises a substance that promotes bone growth.

The term "polymer" refers to a molecule with repeating subunits. The following abbreviations may be used to refer to exemplary known polymers. The abbreviation "DLG" refers to poly(DL-lactide-co-glycolide). The abbreviation "DL" refers to poly(DL-lactide). The abbreviation "LG" refers to poly(L-lactide-co-glycolide). The abbreviation "CL" refers to polycaprolactone. The abbreviation "DLCL" refers to poly(DL-lactide-co-caprolactone). The abbreviation "LCL" refers to poly(L-lactide-co-caprolactone). The abbreviation "G" refers to polyglycolide. The abbreviation "PEG" refers to poly(ethylene glycol). The abbreviation "PLGA" refers to poly(lactide-co-glycolide). The abbreviation "PLA" refers to polyglycolide. The abbreviation "POE" refers to poly(orthoester).

The phrase "release rate profile" refers to the percentage of active ingredient that is released over fixed units of time, e.g., mg/hr, mg/day, mcg/hr, mcg/day, 10% per day for ten days, etc. As persons of ordinary skill know a release rate profile may, but need not, be linear.

"Target tissue site" The term "target tissue site" is intended to mean the location of the tissue to be treated. Typically the placement site of the foam will be the same as the target site to provide for optimal targeted drug delivery. However, the present application also contemplates positioning the foam at a placement site at or near the target site such that the therapeutic agent can be delivered to the surrounding vasculature, which carries the agent to the desired nearby target site. As used herein, the term "at or near" includes embodiments where the placement site and target site are within close proximity. In some embodiments, both sites are within the cranial maxillofacial environment. In some embodiments, if the target tissue site is a larger tissue area or orofacial structure or if it is desired to distribute the growth factor and/or other therapeutic agent over a larger tissue segment, this can be accomplished not only by passive diffusion through the adjacent tissue, but also utilizing convective transport via the nearby vasculature. Convective transport is often much faster than passive diffusion and allows for a more effective and far-reaching drug administration. For those skilled in the art the appropriate placement sites can be easily determined by assessing the course of the principal arteries supplying the head and neck that convey oxygenated blood and nutrition to the cranial maxillofacial tissues.

A "therapeutically effective amount" or "effective amount" is such that when administered, the drug results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug bead, foam and/or component thereof, or as the result of metabolic transformation or dissolution of the therapeutic agent(s) or conjugates of therapeutic agent(s).

The two types of formulations (sustain release and immediate release) may be used in conjunction. For example, one can use a mixture of formulations that provide different release profiles, either by use of different forms of the drug or by mixtures of different formulations of sustained release materials. The sustained release and immediate release may be in one or more of the same beads. In various embodiments, the sustained release and immediate release may be part of separate beads. For example a bolus or immediate release formulation of a growth factor may be placed at or near the target site and a sustain release formulation may also be placed at or near the same site or be provided within the same formulation through a combination of different polymer matrices and/or drug forms. Thus, even after the bolus becomes completely accessible, the sustain release formulation would continue to provide the active ingredient for the intended tissue.

In various embodiments, the drug bead can be designed to cause an initial burst dose of therapeutic agent within the first twenty-four hours after implantation. The phrases "initial burst," "burst effect," and "bolus dose" refer to the release of therapeutic agent from the bead during the first twenty-four hours after the bead comes in contact with an aqueous fluid (e.g., saliva, cerebral spinal fluid, etc.). The "burst effect" is believed to be due to the increased release of therapeutic agent from the bead. In alternative embodiments, the bead is designed to avoid this initial burst effect.

The terms "treating" and "treatment" when used in connection with a disease or condition refer to executing a protocol that may include administering one or more drugs to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient. Some conditions the present application can be used in include treatments of the craniomaxillofacial complex: mouth, jaws, neck, face, skull, such as for example, dentoalveolar surgery (surgery to remove impacted teeth, difficult tooth extractions, extractions on medically compromised patients, bone grafting or preprosthetic surgery to provide better anatomy for the placement of implants, dentures, or other dental prostheses), alveolar ridge defects, osteocondensation in the oral and/or craniomaxillofacial skeleton, guided bone regeneration procedures, procedures after removal of cysts and/or tumors, ablative and/or reconstructive surgery, treatment of craniofacial malformations such as cleft lip or palate or cranial vault malformations such as craniosynostosis, treatment of temporomandibular joint (TMJ), orthognathic surgery, maxillomandibular advancement, surgical correction of correction of facial asymmetry, treat trauma to the oral and maxillofacial region (jaw fractures, cheek bone fractures, nasal fractures, LeFort fracture, skull fractures and eye socket fractures, surgery to insert osseointegrated (bone fused) dental implants or maxillofacial implants for attaching craniofacial prostheses or bone anchored hearing aids or cosmetic surgery limited to the head and neck (rhytidectomy/facelift, blepharoplasty, otoplasty, rhinoplasty, genioplasty, etc.) or the like.

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

In some embodiments, the present application provides an osteogenic composition for implantation in an organism, wherein the osteogenic composition comprises: a porous foam and a polymeric bead. The polymeric bead may be designed for delivering a growth factor at or near the target tissue site. In some embodiments, one of both of the porous foam and polymeric bead are biodegradable, bioerodable and/or bioabsorbable.

Foam

The foam of the present application is utilized as a scaffold for bone and/or cartilage repair, regeneration, and/or augmentation. The foam comprises a biocompatible material and has an open celled microstructure. Typically, the foam provides a 3-D matrix of interconnecting pores, which acts as a pliable, compression resistant scaffold for cell migration. The morphology of the scaffold guides cell migration and cells are able to migrate into or over the scaffold, respectively. The cells then are able to proliferate and synthesize new tissue and form bone and/or cartilage.

The porous foam comprises a plurality of pores. In some embodiments, at least 50% of the pores are between about 100 micrometers and about 300 micrometers at their widest points. In some embodiments, at least 60% of the pores are between about 100 micrometers and about 300 micrometers at their widest points. In some embodiments, at least 70% of the pores are between about 100 micrometers and about 300 micrometers at their widest points. In some embodiments, at least 80% of the pores are between about 100 micrometers and about 300 micrometers at their widest points. In some embodiments, at least 90% of the pores are between about 100 micrometers and about 300 micrometers at their widest points. In some embodiments, at least 95% of the pores are between about 100 micrometers and about 300 micrometers at their widest points. In some embodiments, 100% of the pores are between about 100 micrometers and about 300 micrometers at their widest points.

In some embodiments, at least 50% of the pores are between about 150 micrometers and about 250 micrometers at their widest points. In some embodiments, at least 60% of the pores are between about 150 micrometers and about 250 micrometers at their widest points. In some embodiments, at least 70% of the pores are between about 150 micrometers and about 250 micrometers at their widest points. In some embodiments, at least 80% of the pores are between about 150 micrometers and about 250 micrometers at their widest points. In some embodiments, at least 90% of the pores are between about 150 micrometers and about 250 micrometers at their widest points. In some embodiments, at least 95% of the pores are between about 150 micrometers and about 250 micrometers at their widest points. In some embodiments, 100% of the pores are between about 150 micrometers and about 250 micrometers at their widest points.

The porous foam may comprise poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, or combinations thereof.

In some embodiments, the foam may comprise a resorbable ceramic (e.g., hydroxyapatite, tricalcium phosphate, bioglasses, calcium sulfate, etc.) tyrosine-derived polycarbonate poly(DTE-co-DT carbonate), in which the pendant group via the tyrosine—an amino acid—is either an ethyl ester (DTE) or free carboxylate (DT) or combinations thereof.

In some embodiments, the foam comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the foam may comprise particles of bone-derived materials. The bone-derived material may include one or more of non-demineralized bone particles, demineralized bone particles, lightly demineralized bone particles, and/or deorganified bone particles.

In some embodiments, the foam may be seeded with harvested bone cells or tissue, such as for example, cortical bone, autogenous bone, allogenic bones and/or xenogenic bone. For example, before insertion into the target tissue site, the foam can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the scaffolding provided by the foam, and the foam may be kneaded by hand, thereby obtaining a pliable consistency that may subsequently be gently packed into the target tissue site. The foam provides a malleable, non-water soluble carrier that permits accurate placement and retention of the growth factor at the implantation site.

The foam may contain an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, tissue will infiltrate the foam to a degree of about 50 percent of the foam thickness within about 10 days of implantation of the scaffold. In some embodiments, about 75 percent of the foam thickness will be infiltrated by tissue within about 7 days of implantation of the scaffold. In some embodiments, the foam will be substantially, e.g., about 90 percent or more, submerged in or enveloped by tissue within about 30 days of implantation of the scaffold. In some embodiments, the foam scaffold will be completely submerged in or enveloped by tissue within about 60 days of implantation.

In some embodiments, the foam has a thickness of from 0.25 mm to 3 mm, or from about 0.4 mm to about 2 mm, or 0.4 mm to about 1 mm. Clearly, different tissue defects may require different foam thickness. For example, in some embodiments, the foam is 45-76 mm in length, 25-27 mm width, and 25-27 mm in height for cranial maxillofacial defects.

In some embodiments, the porous foam has a density of between about 1.6 $g/cm^3$, and about 0.05 $g/cm^3$. In some embodiments, the porous composite has a density of between about 1.1 $g/cm^3$, and about 0.07 $g/cm^3$. For example, the density may be less than about 1 $g/cm^3$, less than about 0.7 $g/cm^3$, less than about 0.6 $g/cm^3$, less than about 0.5 $g/cm^3$, less than about 0.4 $g/cm^3$, less than about 0.3 $g/cm^3$, less than about 0.2 $g/cm^3$, or less than about 0.1 $g/cm^3$.

In some embodiments, the porous foam has a porosity of at least about 30%, at least about 50%, at least about 60%, at least about 70%, at least about 90%. The pore may support in growth of cell and/or the formation or remodeling of bone.

In some embodiments, the foam can be pliant, resists compression and is suitable for cranial oral and maxillofacial procedures. The foam can resist compression forces in the range of from about 1 MPa to about 100 MPa. In some embodiments, the foam can resist 1 to 2 MPa forces in procedures such as socket preservations, sinus lifts, and for ridge or sinus augmentation about 35-40 MPa.

The shape of the porous foam may be tailored to the site at which it is to be situated. For example, it may be in the shape of morsels, a cylinder, a block, a wedge, a sheet, etc.

The foam may be made by injection molding, compression molding, blow molding, thermoforming, die pressing, slip casting, electrochemical machining, laser cutting, water-jet machining, electrophoretic deposition, powder injection molding, sand casting, shell mold casting, lost foam casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

In some embodiments, a growth factor and/or therapeutic agent may be disposed on or in the foam by electrospraying, ionization spraying or impregnating, vibratory dispersion (including sonication), nozzle spraying, compressed-air-assisted spraying, brushing and/or pouring. For example, a growth factor such as rhBMP-2 may be disposed on or in the foam cells. In this embodiment, the rhBMP-2 can provide immediate release of the rhBMP-2 as opposed to sustain release of the rhBMP-2 over time.

One or more polymer beads may be disposed on or in the foam or foam cells. In some embodiments, the one or more beads are disposed on or in an outer peripheral surface of the foam. In some embodiments, the one or more beads are disposed on or in the center of the foam. In some embodiments, a plurality of beads are disposed throughout the entire surface of the foam or different layers of the foam. The foam not only functions as a tissue scaffold but also confines the one or more polymer beads to a target tissue site.

Growth Factors

The polymer bead and/or foam may comprise at least one growth factor. These growth factors include osteoinductive agents (e.g., agents that cause new bone growth in an area where there was none) and/or osteoconductive agents (e.g., agents that cause in growth of cells into and/or through the foam). Osteoinductive agents can be polypeptides or polynucleotides compositions. Polynucleotide compositions of the osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art, (See, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo. Preferred embodiments of variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that are included within the bead and/or foam are typically sterile. In a non-limiting method, sterility is readily accomplished for example by filtration through sterile filtration membranes (e.g., 0.2 micron membranes or filters). In one embodiment, the isolated osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12;

BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents include one or more members of the family of Transforming Growth Factor-beta genes ("TGFbetas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP_005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP_004855, as well as mature GDF-15 polypeptides or polynucleotides encoding the same.

In another embodiment, isolated osteoinductive agents include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents include one or more members of any one of the families of Bone Morphogenetic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), as well as mixtures or combinations thereof.

In another embodiment, the one or more isolated osteoinductive agents useful in the bioactive formulation are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and or combination thereof; Osteoprotegerin; TGF-beta-1, TGF-beta-2, TGF-beta-3, or any combination thereof; or any combination of one or more members of these groups.

The concentrations of growth factor can be variable based on the desired length or degree of osteogenic effects desired. Similarly, one of skill in the art will understand that the duration of sustained release can be modified by the manipulation of the compositions comprising the sustained release formulation, such as for example, modifying the percent of polymers found within a sustained release formulation, microencapsulation of the formulation within polymers, including polymers having varying degradation times and characteristics, and layering the formulation in varying thicknesses in one or more degradable polymers. These sustained release formulations can therefore be designed to provide customized time release of growth factors that simulate the natural healing process.

The amount of growth factor, e.g., bone morphogenic protein may be sufficient to bone growth in a cranial bone. In some embodiments, the growth factor is rhBMP-2 and is contained in one or more polymeric beads in an amount of from 1 to 2 mg per cubic centimeter of the osteogenic composition. In some embodiments, the amount of rhBMP-2 morphogenic protein is from 2.0 to 2.5 mg per cubic centimeter of said osteogenic composition.

Additional Therapeutic Agents

The growth factors of the present application may be disposed on or in the foam and/or beads with other therapeutic agents. For example, the growth factor and/or therapeutic agent may be disposed on or in the foam and/or bead by electrospraying, ionization spraying or impregnating, vibratory dispersion (including sonication), nozzle spraying, compressed-air-assisted spraying, brushing and/or pouring.

Exemplary therapeutic agents include but are not limited to IL-1 inhibitors, such Kineret® (anakinra), which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dilhiocarbamate, and other compounds, such as, for example, sulfasalazine.

Examples of therapeutic agents suitable for use also include, but are not limited to an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In addition to the aforementioned polymer, the growth factor may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the bead will be a solid or semi-solid formulation comprises a biocompatible material that can be biodegradable.

Beads

The beads of the present application can be different sizes, shapes and configurations including but not limited to spheroidal, plate, fiber, cuboidal, sheet, rod, ellipsoidal, string, elongated, polyhedral, other regular shapes, irregular shapes or mixtures thereof. In some embodiments, the differently sized and shaped beads may be used in combination with each other.

In some embodiments, beads are provided as they allow micro-particles to be produced in a spherical shape that can contain the growth factor and/or other therapeutic agents. In some embodiments, the dosage of growth factor (e.g., PTH) can be started at 1 µg/kg/day and in the range of 100-150 pg/ml. In some embodiments, the beads can be placed within the entire foam structure.

In some embodiments, the average size of the polymeric beads is less than 5 mm, 4 mm, 3 mm, 2 mm, 1 mm, or 0.5 mm. In some embodiments, at least 90% of the polymeric beads have a diameter of less than 5 mm, 4 mm, 3 mm, 2 mm, 1 mm, or 0.5 mm. In some embodiments all at the polymeric beads have a diameter of less than 5 mm, 4 mm, 3 mm, 2 mm, 1 mm or 0.5 mm.

In various embodiments, the bead will comprise a polymer that is durable within the tissue site for a period of time equal to (for biodegradable components) or greater than (for non-biodegradable components) the planned period of drug delivery. For example, the bead material may have a melting point or glass transition temperature close to or higher than body temperature, but lower than the decomposition or degradation temperature of the therapeutic agent and/or growth factor. However, the pre-determined erosion of the bead material can also be used to provide for slow release of the loaded therapeutic agent(s) and/or growth factor(s).

In some embodiments, the bead may not be biodegradable. For example, the bead may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, PVC, polyurethane, ceramics or combinations thereof. Typically, these types of beads may need to be removed after a certain amount of time.

In some instances, it may be desirable to avoid having to remove the bead after use. In those instances, the bead may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system bead (homogeneous or bulk erosion).

In various embodiments, the bead may comprise a bioerodable, a bioabsorbable, and/or a biodegradable biopolymer that may provide immediate release, or sustained release of the growth factor and/or therapeutic agent. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters (POE), polyaspirins, polyphosphagenes, D,L-lactide, or L-lactide, -caprolactone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, or combinations thereof.

The bead may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the bead is to be placed in the spinal area, in various embodiments, the bead may comprise sterile preservative free material.

Exemplary excipients include but are not limited to mPEG, D-Sorbital, maltodextran, cyclodextrin or combinations thereof. The excipients, when present may for example be present in the beads in an amount of from about 0.05 wt. % to about 85 wt. %.

In some embodiments, the range of the polymer can be 0.1% to 99% w/w or w/v or v/v with the remainder being the active therapeutic ingredient (e.g., growth factor, other therapeutic agent).

Radiographic markers can be included on the polymeric bead and/or osteogenic composition to permit the user to position the bead accurately into the target site of the patient. These radiographic markers will also permit the user to track movement and degradation of the bead and/or foam at the site over time. In this embodiment, the user may accurately position the bead and/or foam in the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles. In various embodiments, the radiographic marker could be a spherical shape or a ring around the bead and/or foam.

The polymer that may be used in forming the polymeric bead may for example be monomers, pre-polymers; oligomers; polymers, cross-linked polymers, partially polymerized polymers, partially cross-linked polymers and combinations thereof. Exemplary polymers include but are not limited to, poly(lactide), poly(glycolide), poly(lactide-co-glycolide), L-lactide-co-glycolide, poly(L-lactide-co-glycolide), polycaprolactonel, polyurethane, polycarbonates, polyarylates, poly(propylene fumarates), polyphosphazines or combinations thereof.

In various embodiments, the molecular weight of the bead can be varied by many methods known in the art. The molecular weight of the polymer can be varied to regulate the release rate profile and/or delivery duration of the active ingredient. In general, as the molecular weight of the polymer increases, one or more of the following occurs: the burst index is lower, the release profile is flatter and/or the duration of delivery is longer. The choice of method to vary molecular weight is typically determined by the composition of bead and/or foam (e.g., polymer, versus non-polymer). For example in various embodiments, when the bead comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time. By way of a non-limiting example, the polymer make up may comprise from 50:50 PLGA to 100 PLA and the molecular weight range may be from 0.45 to 0.8 dI/g.

Additionally, by varying the comonomer ratio of the various monomers that form a polymer (e.g., the L/G/CL or G/CL ratio for a given polymer) there will be a resulting bead composition having a regulated burst index and duration of delivery. For example, a bead composition having a polymer with a L/G ratio of 50:50 has a short duration of delivery ranging from about two days to about one month; a bead composition having a polymer with a L/G ratio of 65:35 has a duration of delivery of about two months; a bead composition having a polymer with a L/G ratio of 75:25 or L/CL ratio of 75:25 has a duration of delivery of about three months to about four months; a bead composition having a polymer ratio with a L/G ratio of 85:15 has a duration of delivery of about five months; a bead composition having a polymer with a L/CL ratio of 25:75 or PLA has a duration of delivery greater than or equal to six months; a bead composition having a terpolymer of CL/G/L with G greater than 50% and L greater than 10% has a duration of delivery of about one month and a bead composition having a terpolymer of CL/G/L with G less than 50% and L less than 10% has a duration months up to six months. In general, increasing the G content relative to the CL content shortens the duration of delivery whereas increasing the CL content relative to the G content lengthens the duration of delivery.

Thus, bead compositions having a blend of polymers having different molecular weights, end groups and comonomer ratios can be used to create a bead formulation having a lower burst index and a regulated duration of delivery.

Kits

In various embodiments, a kit is provided that may include additional parts along with the drug bead and/or foam combined together to be used to implant the osteogenic composition. The kit may include the osteogenic composition in a first compartment. The second compartment may include a canister holding the drug bead and any other instruments needed for the localized drug delivery. A third compartment may include gloves, drapes, wound dressings and other procedural supplies for maintaining sterility of the implanting process, as well as an instruction booklet. A fourth compartment may include additional tools for implantation. A fifth compartment may comprise an agent for radiographic imaging. Each tool may be separately packaged in a plastic pouch that is radiation sterilized. A cover of the kit may include illustrations of the implanting procedure and a clear plastic cover may be placed over the compartments to maintain sterility.

Methods for Treating

In various embodiments, a method for delivering a growth factor to a site of a patient is provided, the method comprising delivering an osteogenic composition at or near a target tissue site.

In some embodiments, the present application provides a method for inducing bone formation, said method comprising the step of implanting at a target tissue site accessible to migrating progenitor cells of said organism, the osteogenic compositions described above. Through these methods one may accelerate allograft, autograft, or xenograft repair in an organism. For example, the method may comprise the step of implanting at a locus in need of replacement bone, an osteogenic composition comprising: a porous foam, wherein said porous foam contains a plurality of pores that are between about 100 mircometers and about 350 micrometers at their widest points; and a bead, wherein said bead comprises a growth factor, and a polymer.

By way of example, the organism to which the osteogenic composition is administered may be a mammal, e.g., human. The organism may be suffering from a bone fracture or a bone defect. Furthermore, the osteogenic composition may used to treat a genetic disease, congenital abnormality, a fracture, an iatrogenic defect, a bone cancer, a bone metastasis, an inflammatory disease, an autoimmune disease, a metabolic disease, or a degenerative bone disease.

Exemplary conditions the present application can be used in include treatments of the craniomaxillofacial complex: mouth, jaws, neck, face, skull, and include: dentoalveolar surgery (surgery to remove impacted teeth, difficult tooth extractions, extractions on medically compromised patients, bone grafting or preprosthetic surgery to provide better anatomy for the placement of implants, dentures, or other dental prostheses), alveolar ridge defects, osteocondensation in the oral and/or cranio-maxillofacial skeleton, guided bone regeneration procedures, procedures after removal of cysts and/or tumors, ablative and/or reconstructive surgery, treatment of craniofacial malformations such as cleft lip and palate and cranial vault malformations such as craniosynostosis, treatment of temporomandibular joint (TMJ), orthognathic surgery, maxillomandibular advancement, surgical correction of correction of facial asymmetry, treatment of trauma to the oral and maxillofacial region (jaw fractures, cheek bone fractures, nasal fractures, LeFort fracture, skull fractures and eye socket fractures, surgery to insert osseointegrated (bone fused) dental implants and maxillofacial implants for attaching craniofacial prostheses and bone anchored hearing aids or cosmetic surgery limited to the head and neck (rhytidectomy/facelift, blepharoplasty, otoplasty, rhinoplasty, genioplasty, etc.) or the like.

Methods of Making

The polymer beads of the present application may be made by mixing a growth factor with a polymer under at a temperature sufficient to facilitate mixing, and under sufficient agitation or stirring conditions to facilitate mixing. Other active or inactive ingredients described above may be included in the mixture.

In various embodiments, the drug bead comprising the growth factor can be made by combining a biocompatible polymer and a therapeutically effective amount of the growth factors and forming the implantable drug bead from the combination. This bead can then be combined with the foam for delivery to a target tissue site.

Various techniques are available for forming at least a portion of a drug bead from the biocompatible polymer(s), growth factor(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or growth factor. The particular solvent species that makes up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques or electrostatic techniques. Where appropriate, techniques such as those listed above can be repeated or combined to build up the bead to obtain the desired release rate and desired thickness.

In various embodiments, a solution containing solvent and biocompatible polymer are combined and placed in a mold of the desired bead size and shape. In this way, polymeric regions, including barrier layers, lubricious layers, and so forth can be formed. If desired, the solution can further comprise, one or more of the following: other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed growth factor is applied to a pre-existing polymeric region, which can be formed using a variety of techniques including solution processing and thermoplastic processing techniques, whereupon the growth factor and/or therapeutic agent is imbibed into the polymeric region.

Thermoplastic processing techniques for forming the bead or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the growth factor(s), optional additional therapeutic agent(s), radiographic agent(s), and so forth. The resulting mixture is then shaped into an implantable drug bead. The mixing and shaping operations may be performed using any of the conventional devices known in the art for such purposes.

During thermoplastic processing, there exists the potential for the growth factor(s) to degrade, for example, due to elevated temperatures and/or mechanical shear that are associated with such processing. For example, certain growth factors may undergo substantial degradation under ordinary thermoplastic processing conditions. Hence, processing can be performed under modified conditions, which prevent the substantial degradation of the growth factor(s). Although it is understood that some degradation may be unavoidable during thermoplastic processing, degradation is generally limited to 10% or less. Among the processing conditions that may be controlled during processing to avoid substantial degradation of the growth factor(s) and/or therapeutic agent(s) are temperature, applied shear rate, applied shear stress, residence time of the mixture containing the growth factor(s) and/or therapeutic agent(s), and the technique by which the polymeric material, growth factor(s) and/or therapeutic agent(s) are mixed.

Mixing or compounding a biocompatible polymer with growth factor(s) and/or therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), growth factors, etc.) to form a mixture. A common way of doing so is to apply mechanical shear to a mixture of the biocompatible polymer(s) growth factor(s), therapeutic agent(s) and/or additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the growth factor and/or therapeutic agent, if it were present. This precompounded material is then mixed with therapeutic agent under conditions of lower temperature and mechanical shear, and the resulting mixture is shaped into the growth factor containing drug bead. Conversely, in another embodiment, the biocompatible polymer can be precompounded with the growth factor(s) and/or therapeutic agent(s) under conditions of reduced temperature and mechanical shear. This precompounded material is then mixed with, for example, a radio-opacifying agent, also under conditions of reduced temperature and mechanical shear, and the resulting mixture is shaped into the drug bead.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a bead is formed comprising PLGA or PLA polymer, a radio-opacifying agent (e.g., bismuth subcarbonate), and a growth factor(s) prone to degradation by heat and/or mechanical shear (e.g., rhBMP-2), in various embodiments, the PGLA or PLA can be premixed with the radio-opacifying agent at temperatures of about, for example, 150° C. to 170° C. The growth factor is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s) and/or growth factor. For instance, the therapeutic agent and/or growth factor and premixed composition can be mixed/compounded using a twin screw extruder at substantially lower temperatures (e.g., 35-40° C.), and using substantially reduced volumetric output (e.g., less than 30% of full capacity, which generally corresponds to a volumetric output of less than 200 cc/min). It is noted that this processing temperature is well below the degradation points of certain growth factors and/or therapeutic agents, because processing at or above these temperatures may result in substantial therapeutic agent degradation. It is further noted that in certain embodiments, the processing temperature will be below the melting point of all therapeutic compounds within the composition. After compounding, the resulting bead is shaped into the desired size, also under conditions of reduced temperature and shear.

In other embodiments, biodegradable polymer(s) and one or more growth factor(s) and/or therapeutic agent(s) are premixed using non-thermoplastic techniques. For example, the biocompatible polymer can be dissolved in a solvent system containing one or more solvent species. Any desired agents (for example, a radio-opacifying agent, a growth factor, or both radio-opacifying agent and growth factor) can also be dissolved or dispersed in the solvents system. Solvent is then removed from the resulting solution/dispersion, forming a solid bead.

As another example, the growth factor can be dissolved or dispersed in a solvent system, which is then applied to a pre-existing drug bead (the pre-existing drug bead can be formed using a variety of techniques including solution and thermoplastic processing techniques, and it can comprise a variety of additives including a radio-opacifying agent and/or viscosity enhancing agent), whereupon the growth factor is imbibed on or in the drug bead.

Typically, an extrusion processes may be used to form the drug bead comprising a biocompatible polymer(s), growth factor(s) and/or therapeutic agent(s) and radio-opacifying agent(s). Co-extrusion may also be employed, which is a shaping process that can be used to produce a drug bead comprising the same or different layers or regions (for example, a structure comprising one or more polymeric matrix layers or regions) that have permeability to fluids to allow immediate and/or sustained drug release. Multi-region beads can also be formed by other processing and shaping techniques such as co-injection or sequential injection molding technology.

In various embodiments, the bead that may emerge from the thermoplastic processing is cooled. Examples of cooling processes include air cooling and/or immersion in a cooling bath. In some embodiments, a water bath is used to cool the extruded bead. However, where a water-soluble therapeutic agent such as growth factors are used, the immersion time should be held to a minimum to avoid unnecessary loss of therapeutic agent into the bath.

In various embodiments, the drug bead can be prepared by mixing or spraying the drug with the polymer and then molding the bead to the desired shape. In various embodiments, growth factors are used and mixed or sprayed with the PLGA or PEG550 polymer, and the resulting bead may be formed by extrusion and dried.

The drug bead may also comprise combining a biocompatible polymer and a therapeutically effective amount of at least one growth factor(s) with one or more agent(s) analgesic agent or pharmaceutically acceptable salt thereof, at least one anti-inflammatory agent or pharmaceutically acceptable salt thereof and forming the implantable drug bead from the combination.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An osteogenic composition for implantation at or near a target tissue site, the osteogenic composition having no demineralized bone particles and comprising:
    polymeric beads comprising immediate release beads and sustained release beads for delivering an isolated osteoinductive agent comprising a sterile growth factor at or near the target tissue site, the polymeric beads being biodegradable and synthetic; the polymeric beads comprising the growth factor, mPEG as an excipient in an amount of from about 0.05 wt. % to about 85 wt. %, a viscosity enhancing agent, degradation/release modifiers and sterile preservative free material; and
    a porous foam comprising layers for confining the polymeric beads at or near the target tissue site, wherein the immediate release beads and sustained release beads are disposed throughout the layers of the foam, the porous foam being biodegradable and containing a plurality of pores having a size between about 100 micrometers and about 350 micrometers at their widest points; and
    wherein the growth factor comprises bone morphogenic protein;
    wherein the amount of bone morphogenic protein is from 1 to 2 mg per cubic centimeter of said osteogenic composition;
    wherein the foam has a density of between about 0.2 g/cm$^3$ to about 1.1 g/cm$^3$; and
    wherein the porous foam comprises seeded bone cells or tissue.

2. An osteogenic composition of claim 1, wherein the porous foam comprises at least one of collagen, a resorbable polymer, gelatin, a resorbable ceramic or combinations thereof.

3. An osteogenic composition of claim 1, wherein the bone morphogenic protein is bone morphogenic protein-2 to promote bone growth in a cranial bone.

4. An osteogenic composition of claim 1, wherein the polymeric beads comprise poly(lactide-co-glycolide) (PLGA).

5. An osteogenic composition of claim 1, wherein said beads have a diameter of 0.5 to 1.0 mm.

6. An osteogenic composition of claim 1, wherein said beads have a diameter of 1.0 to 3.0 mm.

7. An osteogenic composition of claim 1, wherein said beads have a diameter of 3.0 to 5.0 mm.

8. An osteogenic composition of claim 1, wherein the polymeric beads do not contain ceramic.

9. An osteogenic composition of claim 1, wherein the bone morphogenic protein is bone morphogenic protein-2 and the polymer beads are coated or impregnated with bone morphogenic protein-2.

10. An osteogenic composition of claim 1, wherein the foam has a porosity of at least about 50%.

11. An osteogenic composition of claim 10, wherein the foam has a porosity of at least about 70%.

12. An osteogenic composition of claim 11, wherein the foam has a porosity of at least about 90%.

13. A method for inducing bone formation, said method comprising the step of implanting at a target tissue site accessible to migrating progenitor cells, the osteogenic composition of claim 1.

14. An osteogenic composition for implantation at or near a target tissue site, the osteogenic composition having no demineralized bone particles and comprising:
    one or more polymeric beads comprising immediate release beads and sustained release beads containing: an effective amount of an isolated osteoinductive agent comprising a sterile growth factor comprising bone morphogenic protein, mPEG as an excipient in an amount of from about 0.05 wt. % to about 85 wt. %, a viscosity enhancing agent, degradation/release modifiers and sterile preservative free material, said one or more polymeric beads being synthetic, biodegradable and less than 3.0 mm in diameter and adapted to deliver the growth factor at or near the target tissue site; and
    a porous foam comprising layers for confining the one or more polymeric beads at or near the target tissue site, wherein the immediate release beads and sustained release beads are disposed throughout the layers of the foam, the porous foam being biodegradable and containing a plurality of pores having a size of between about 100 micrometers and about 350 micrometers to allow tissue growth at the target tissue site; and
    wherein the amount of bone morphogenic protein is from 1 to 2 mg per cubic centimeter of said osteogenic composition;
    wherein the porous foam has a density of between about 0.2 g/cm$^3$ to about 1.1 g/cm$^3$; and
    wherein the porous foam comprises seeded bone cells or tissue.

15. A method for inducing bone formation, said method comprising the step of implanting at a target tissue site accessible to migrating progenitor cells of said organism, the osteogenic composition of claim 14.

16. An osteogenic composition for implantation at or near a target tissue site, the osteogenic composition having no demineralized bone particles and comprising:
    one or more polymeric beads comprising immediate release beads and sustained release beads containing an effective amount of an isolated osteoinductive agent comprising a sterile growth factor comprising bone morphogenic protein, mPEG as an excipient in an amount of from about 0.05 wt. % to about 85 wt. %, a viscosity enhancing agent, degradation/release modifiers and sterile preservative free material, said one or more polymeric beads being synthetic, biodegradable and less than 3.0 mm in diameter and adapted to deliver the growth factor at or near the target tissue site; and
    a porous foam comprising layers for confining the one or more polymeric beads at or near the target tissue site, wherein the immediate release beads and sustained release beads are disposed throughout the layers of the foam, the porous foam being biodegradable and containing a plurality of pores having a size of between about 100 micrometers and about 350 micrometers to allow tissue growth at the target tissue site; and
wherein the amount of bone morphogenic protein is from 1 to 2 mg per cubic centimeter of said osteogenic composition;
wherein the porous foam has a density of between about 0.2 g/cm$^3$ to about 1.1 g/cm$^3$;
wherein the porous foam has a thickness of between 0.25 mm to about 2 mm; and
wherein the porous foam comprises seeded bone cells or tissue.

* * * * *

UNITED STATES PATENT AND TRADEMARK OFFICE
CERTIFICATE OF CORRECTION

PATENT NO. : 9,492,375 B2  
APPLICATION NO. : 12/178497  
DATED : November 15, 2016  
INVENTOR(S) : Scifert Page 1 of 1

It is certified that error appears in the above-identified patent and that said Letters Patent is hereby corrected as shown below:

In the Specification

In Column 7, Line 2, delete "micrometersand" and insert -- micrometers and --, therefor.

In the Claims

Column 21, Line 50, in Claim 1, delete "hone" and insert -- bone --, therefor.

Signed and Sealed this
Twenty-first Day of February, 2017

Michelle K. Lee
*Director of the United States Patent and Trademark Office*